US009994899B2

(12) United States Patent
Nyström et al.

(10) Patent No.: US 9,994,899 B2
(45) Date of Patent: Jun. 12, 2018

(54) METHOD TO DETERMINE DNA MISMATCH REPAIR FUNCTION

(75) Inventors: Minna Nyström, Helsingin yliopisto (FI); Minttu Kansikas, Helsingin yliopisto (FI); Päivi Peltomäki, Helsingin yliopisto (FI)

(73) Assignee: HELSINGIN YLIOPISTO, Helsingin Yliopisto (FI)

( * ) Notice: Subject to any disclaimer, the term of this patent is extended or adjusted under 35 U.S.C. 154(b) by 82 days.

(21) Appl. No.: 14/128,049

(22) PCT Filed: Jun. 29, 2012

(86) PCT No.: PCT/EP2012/062708
§ 371 (c)(1),
(2), (4) Date: Mar. 4, 2014

(87) PCT Pub. No.: WO2013/004618
PCT Pub. Date: Jan. 10, 2013

(65) Prior Publication Data
US 2014/0220559 A1 Aug. 7, 2014

Related U.S. Application Data

(60) Provisional application No. 61/503,735, filed on Jul. 1, 2011.

(30) Foreign Application Priority Data

Jul. 1, 2011 (FI) ...................................... 20115709

(51) Int. Cl.
*C12Q 1/68* (2018.01)
*C12P 19/34* (2006.01)
(Continued)

(52) U.S. Cl.
CPC .......... *C12Q 1/6883* (2013.01); *C12Q 1/6827* (2013.01); *C12Q 1/6886* (2013.01); *C12Q 2600/156* (2013.01)

(58) Field of Classification Search
USPC ......... 435/6.1, 6.11, 91.2, 183; 436/94, 501; 536/23.1, 24.3, 24.33
See application file for complete search history.

(56) References Cited

FOREIGN PATENT DOCUMENTS

WO    2008142521 A2    11/2008

OTHER PUBLICATIONS

Peltomaki, Deficient DNA mismatch repair: a common etiologic factor for colon cancer. Cell Research, 18, 85-98, 2008.*
(Continued)

*Primary Examiner* — Frank Lu
(74) *Attorney, Agent, or Firm* — Nath, Goldberg & Meyer; Joshua B. Goldberg; Tanya E. Harkins

(57) ABSTRACT

This invention relates to a quantitative method for determining whether a human subject has an impaired DNA mismatch repair function; providing a diagnostic sample taken from said human and producing a nuclear extract from said sample; providing MMR proficient and MMR deficient nuclear extracts as positive and negative controls, respectively; combining each nuclear extract with at least one mismatch bearing substrate DNA molecule; performing a mismatch repair assay; and determining whether said sample nuclear extract is capable of repairing said substrate DNA molecule; wherein said sample comprises normal, non-malignant constitutive cells, such as fibroblasts. The invention further relates to a kit providing necessary reagents for use in said method.

4 Claims, 6 Drawing Sheets

(51) Int. Cl.
C07H 21/02 (2006.01)
C07H 21/04 (2006.01)

(56) References Cited

OTHER PUBLICATIONS

"Gene expression" from Wikipedia, the free encyclopedia. Printed on Jun. 10, 2016.*
Lynch syndrome from Cancer.Net. Printed on Jun. 10, 2016.*
"DNA mismatch repair" from Wikipedia, the free encyclopedia. Printed on Nov. 25, 2015.*
Thompson, et al., "Application of a five-tiered scheme for standardized classification of 2,360 unique mismatch repair gene variants lodged on the InSiGHT locus-specific database", Nat Genet., vol. 46, No. 2, pp. 107-115, Feb. 2014.
Tricarico, et al., "Assessment of the InSiGHT Interpretation Criteria for the Clinical Classification of 24 MLH1 and MSH2 Gene Variants", Human Mutation, vol. 38, No. 1, pp. 64-77, 2017.
Bennett et al. "Mismatch Repair in Extracts of Werner Syndrome Cell Lines", Cancer Research, 57, 2956-2960, 1997.
Boyer et al. "Microsatellite Instability, Mismatch Repair Deficiency, and Genetic Defects in Human Cancer Cell Lines", Cancer Research, 55, 6063-6070, 1995.
Ciotta et al. "Increased Somatic Recombination in Methylation Tolerant Human Cells with Defective DNA Mismatch Repair", Journal of Molecular Biology, 276, 705-719, 1998.
Couch et al. "Assessment of Functional Effects of Unclassified Genetic Variants", Human Mutation, 29(11), 1314-1326, 2008.
Gu et al. "Mismatch Repair Deficiency in Hematological Malignancies with Microsatellite Instability", Oncogene, 21, 5758-5764, 2002.
Jarvinen et al. "Controlled 15-Year Trial on Screening for Colorectal Cancer in Families with Hereditary Nonpolyposis Colorectal Cancer", Gastroenterology, 118, 829-834, 2000.
Kansikas et al. "Verification of the Three-Step Model in Assessing the Pathgenicity of Mismatch Repair Gene Variants", Human Mutation, 2010.
Kantelinen et al. "MutSbeta exceeds MutSalpha in dinucleotide loop repair", British Journal of Cancer, 2010, 1-6.
Kantelinen et al. "A putative Lynch syndrome family carrying MSH2 and MSH6 variants of uncertain significance—functional analysis reveals the pathogenic one", Familial Cancer, 10, 2011, 515-520.
Kariola et al. "Functional analysis of MSH6 mutations linked to kindreds with putative hereditary non-polyposis colorectal cancer syndrome", Human Molecular Genetics, 11(11), 2002, 1303-1310.
Lahue et al. "DNA Mismatch Correction in a Defined System", Science, vol. 245, downloaded Dec. 9, 2013.
McDaid et al. "MHLI mediates PARP-dependent cell death in response to the methylating agent N-methyl-N-nitrosourea", British Journal of Cancer, 101, 2009, 441-451.
Nystrom-Lahti et al. "Functional Analysis of MHLI Mutations Linked to Hereditary Nonpolyposis Colon Cancer", Genes, Chromosomes and Cancer, 33, 2003, 160-167.
Pino et al. "Application of Molecular Diagnostics for the Detection of Lynch Syndrome", Expert Rev Mol Diagn., 10(5), 2010, 651-665.
Wang et al. "Mismatch Repair in Human Nuclear Extracts", The Journal of Biological Chemistry, 277(29), 2002, 26136-26142.
Search Report issued in Finnish Patent Application No. 20115709 dated Dec. 4, 2012.

* cited by examiner

SEQUENCE LISTING

```
<160> NUMBER OF SEQ ID NOS: 3

<210> SEQ ID NO 1
<211> LENGTH: 3192
<212> TYPE: DNA
<213> ORGANISM: Artificial sequence
<220> FEATURE:
<221> NAME/KEY: misc_feature
<222> LOCATION: (3154)..(3159)
<223> OTHER INFORMATION: BgIII restriction site, Plasmid

<400> SEQUENCE: 1
tatagtgagt cgtattacaa ttcactggcc gtcgttttac aacgtcgtga ctgggaaaac      60
cctggcgtta cccaacttaa tcgccttgca gcacatcccc ctttcgccag ctggcgtaat     120
agcgaagagg cccgcaccga tcgcccttcc caacagttgc gcagcctgaa tggcgaatgg     180
acgcgccctg tagcggcgca ttaagcgcgg cgggtgtggt ggttacgcgc agcgtgaccg     240
```

-continued

```
ctacacttgc cagcgcccta gcgcccgctc ctttcgcttt cttcccttcc tttctcgcca    300
cgttcgccgg cttccccgt caagctctaa atcggggct cccttaggg ttccgattta       360 gtgctttacg gcacctcgac cccaaaaaac ttgattaggg tgatggttca cgtagtgggc    420
catcgccctg atagacggtt tttcgcccctt tgacgttgga gtccacgttc tttaatagtg   480
gactcttgtt ccaaactgga acaacactca accctatctc ggtctattct tttgatttat   540
aagggatttt gccgatttcg gcctattggt taaaaatga gctgatttaa caaaattta     600 acgcgaattt taacaaaata ttaacgctta caatttcctg atgcggtatt ttctccttac    660
gcatctgtgc ggtatttcac accgcatatg gtgcactctc agtacaatct gctctgatgc    720
cgcatagtta agccagcccc gacacccgcc aacacccgct gacgcgccct gacgggcttg    780
tctgctcccg gcatccgctt acagacaagc tgtgaccgtc tccgggagct gcatgtgtca    840
gaggttttca ccgtcatcac cgaaacgcgc gagacgaaag ggcctcgtga tacgcctatt    900
tttataggtt aatgtcatga taataatggt ttcttagacg tcaggtggca cttttcgggg    960
aaatgtgcgc ggaaccccta tttgtttatt tttctaaata cattcaaata tgtatccgct    1020
catgagacaa taaccctgat aaatgcttca ataatattga aaaggaaga gtatgagtat     1080 tcaacatttc cgtgtcgccc ttattccctt ttttgcggca ttttgccttc ctgttttgc    1140 tcacccagaa acgctggtga agtaaaaga tgctgaagat cagttgggtg cacgagtggg    1200
ttacatcgaa ctggatctca acagcggtaa gatccttgag agttttcgcc ccgaagaacg    1260
ttttccaatg atgagcactt ttaaagttct gctatgtggc gcggtattat cccgtattga    1320
cgccgggcaa gagcaactcg gtcgccgcat acactattct cagaatgact tggttgagta    1380
ctcaccagtc acagaaaagc atcttacgga tggcatgaca gtaagagaat tatgcagtgc    1440
tgccataacc atgagtgata acactgcggc caacttactt ctgacaacga tcggaggacc    1500
gaaggagcta accgcttttt tgcacaacag ggggatcatg taactcgcct tgatcgttgg    1560
gaaccggagc tgaatgaagc cataccaaac gacgagcgtg acaccacgat gcctgtagca    1620
atggcaacaa cgttgcgcaa actattaact ggcgaactac ttactctagc ttcccggcaa    1680
caattaatag actggatgga ggcggataaa gttgcaggac cacttctgcg ctcggccctt    1740
ccggctggct ggtttattgc tgataaatct ggagccggtg agcgtgggtc tcgcggtatc    1800
attgcagcac tggggccaga tggtaagccc tcccgtatcg tagttatcta cacgacgggg    1860
agtcaggcaa ctatggatga acgaaataga cagatcgctg agataggtgc ctcactgatt    1920
aagcattggt aactgtcaga ccaagtttac tcatatatac tttagattga tttaaaactt    1980 cattttaat ttaaaaggat ctaggtgaag atccttttg ataatctcat gaccaaaatc     2040
ccttaacgtg agttttcgtt ccactgagcg tcagacccg tagaaaagat caaaggatct    2100
tcttgagatc ctttttttct gcgcgtaatc tgctgcttgc aaacaaaaaa accaccgcta    2160
ccagcggtgg tttgtttgcc ggatcaagag ctaccaactc tttttccgaa ggtaactggc    2220
ttcagcagag cgcagatacc aaatactgtt cttctagtgt agccgtagtt aggccaccac    2280
ttcaagaact ctgtagcacc gcctacatac ctcgctctgc taatcctgtt accagtggct    2340
gctgccagtg gcgataagtc gtgtcttacc gggttggact caagacgata gttaccggat    2400
aaggcgcagc ggtcgggctg aacggggggt tcgtgcacac agcccagctt ggagcgaacg    2460
acctacaccg aactgagata cctacagcgt gagctatgag aaagcgccac gcttcccgaa    2520
gggagaaagg cggacaggta tccggtaagc ggcagggtcg gaacaggaga gcgcacgagg    2580
gagcttccag ggggaaacgc ctggtatctt tatagtcctg tcgggtttcg ccacctctga    2640
```

```
cttgagcgtc gattttgtgt gatgctcgtca gggggggcgga gcctatggaa aaacgccagc    2700
aacgcggcct ttttacggtt cctggccttt tgctggcctt ttgctcacat gttctttcct    2760
gcgttatccc ctgattctgt ggataaccgt attaccgcct ttgagtgagc tgataccgct    2820
cgccgcagcc gaacgaccga gcgcagcgag tcagtgagcg aggaagcgga gagcgccca    2880 atacgcaaac cgcctctccc cgcgcgttgg ccgattcatt aatgcagctg gcacgacagg    2940
tttcccgact ggaaagcggg cagtgagcgc aacgcaatta atgtgagtta gctcactcat    3000
taggcacccc aggctttaca ctttatgctt ccggctcgta tgttgtgtgg aattgtgagc    3060
ggataacaat ttcacacagg aaacagctat gaccatgatt acgccaagct atttaggtga    3120
cactatagaa tactcaagct tactacttga gggagatctc taggcttgca tggagcggcc    3180
gccaattcgc cc                                                         3192

<210> SEQ ID NO 2
<211> LENGTH: 3192
<212> TYPE: DNA
<213> ORGANISM: Artificial sequence
<220> FEATURE:
<221> NAME/KEY: misc_feature
<222> LOCATION: (34)..(39)
<223> OTHER INFORMATION: Incomplete BglII restriction site, Plasmid

<400> SEQUENCE: 2
gggcgaattg gcggccgctc catgcaagcc tagggatctc cctcaagtag taagcttgag      60
tattctatag tgtcacctaa atagcttggc gtaatcatgg tcatagctgt ttcctgtgtg     120
aaattgttat ccgctcacaa ttccacacaa catacgagcc ggaagcataa agtgtaaagc     180
ctggggtgcc taatgagtga gctaactcac attaattgcg ttgcgctcac tgcccgcttt     240
ccagtcggga aacctgtcgt gccagctgca ttaatgaatc ggccaacgcg cggggagagg     300
cggtttgcgt attgggcgct cttccgcttc ctcgctcact gactcgctgc gctcggtcgt     360
tcggctgcgg cgagcggtat cagctcactc aaaggcggta atacggttat ccacagaatc     420
aggggataac gcaggaaaga acatgtgagc aaaaggccag caaaaggcca ggaaccgtaa     480
aaaggccgcg ttgctggcgt ttttccatag gctccgcccc cctgacgagc atcacaaaaa     540
tcgacgctca agtcagaggt ggcgaaaccc gacaggacta taaagatacc aggcgtttcc     600
ccctggaagc tccctcgtgc gctctcctgt tccgaccctg ccgcttaccg gatacctgtc     660
cgcctttctc ccttcgggaa gcgtggcgct ttctcatagc tcacgctgta ggtatctcag     720
ttcggtgtag gtcgttcgct ccaagctggg ctgtgtgcac gaaccccccg ttcagcccga     780
ccgctgcgcc ttatccggta actatcgtct tgagtccaac ccggtaagac acgacttatc     840
gccactggca gcagccactg gtaacaggat tagcagagcg aggtatgtag gcggtgctac     900
agagttcttg aagtggtggc ctaactacgg ctacactaga agaacagtat ttggtatctg     960
cgctctgctg aagccagtta ccttcggaaa aagagttggt agctcttgat ccggcaaaca    1020
aaccaccgct ggtagcggtg gtttttttgt ttgcaagcag cagattacgc gcagaaaaaa    1080
aggatctcaa gaagatcctt tgatcttttc tacgggtct gacgctcagt ggaacgaaaa     1140
ctcacgttaa gggattttgg tcatgagatt atcaaaaagg atcttcacct agatcctttt    1200
aaattaaaaa tgaagtttta atcaatcta agtatatat gagtaaactt ggtctgacag    1260
ttaccaatgc ttaatcagtg aggcaccat ctcagcgatc tgtctatttc gttcatccat    1320
agttgcctga ctccccgtcg tgtagataac tacgatacgg gagggcttac catctggccc    1380
```

```
cagtgctgca atgataccgc gagacccacg ctcaccggct ccagatttat cagcaataaa    1440
ccagccagcc ggaagggccg agcgcagaag tggtcctgca actttatccg cctccatcca    1500
gtctattaat tgttgccggg aagctagagt aagtagttcg ccagttaata gtttgcgcaa    1560
cgttgttgcc attgctacag gcatcgtggt gtcacgctcg tcgtttggta tggcttcatt    1620
cagctccggt tcccaacgat caaggcgagt tacatgatcc ccctgttgtg caaaaaagcg    1680
gttagctcct tcggtcctcc gatcgttgtc agaagtaagt tggccgcagt gttatcactc    1740
atggttatgg cagcactgca taattctctt actgtcatgc catccgtaag atgcttttct    1800
gtgactggtg agtactcaac caagtcattc tgagaatagt gtatgcggcg accgagttgc    1860
tcttgcccgg cgtcaatacg ggataatacc gcgccacata gcagaacttt aaaagtgctc    1920
atcattggaa aacgttcttc ggggcgaaaa ctctcaagga tcttaccgct gttgagatcc    1980
agttcgatgt aacccactcg tgcacccaac tgatcttcag catctttac tttcaccagc     2040 gtttctgggt gagcaaaaac aggaaggcaa aatgccgcaa aaaagggaat aagggcgaca    2100
cggaaatgtt gaatactcat actcttcctt tttcaatatt attgaagcat ttatcagggt    2160
tattgtctca tgagcggata catatttgaa tgtatttaga aaaataaaca ataggggtt     2220 ccgcgcacat ttccccgaaa agtgccacct gacgtctaag aaaccattat tatcatgaca    2280
ttaacctata aaaataggcg tatcacgagg ccctttcgtc tcgcgcgttt cggtgatgac    2340
ggtgaaaacc tctgacacat gcagctcccg gagacggtca cagcttgtct gtaagcggat    2400
gccgggagca gacaagcccg tcagggcgcg tcagcgggtg ttggcgggtg tcggggctgg    2460
cttaactatg cggcatcaga gcagattgta ctgagagtgc accatatgcg gtgtgaaata    2520
ccgcacagat gcgtaaggag aaaataccgc atcaggaaat tgtaagcgtt aatattttgt    2580
taaaattcgc gttaaatttt tgttaaatca gctcatttt taaccaatag gccgaaatcg    2640
gcaaaatccc ttataaatca aaagaataga ccgagatagg gttgagtgtt gttccagttt    2700
ggaacaagag tccactatta agaacgtgg actccaacgt caaagggcga aaaccgtct     2760 atcagggcga tggcccacta cgtgaaccat cacccctaatc aagtttttg gggtcgaggt    2820 gccgtaaagc actaaatcgg aaccctaaag ggagccccg atttagagct tgacggggaa    2880
agccggcgaa cgtggcgaga aaggaaggga agaaagcgaa aggagcgggc gctagggcgc    2940
tggcaagtgt agcggtcacg ctgcgcgtaa ccaccacacc cgccgcgctt aatgcgccgc    3000
tacagggcgc gtccattcgc cattcaggct gcgcaactgt tgggaagggc gatcggtgcg    3060
ggcctcttcg ctattacgcc agctggcgaa agggggatgt gctgcaaggc gattaagttg    3120
ggtaacgcca gggttttccc agtcacgacg ttgtaaaacg acggccagtg aattgtaata    3180
cgactcacta ta                                                       3192
```

<210> SEQ ID NO 3
<211> LENGTH: 3191
<212> TYPE: DNA
<213> ORGANISM: Artificial Sequence
<220> FEATURE:
<221> NAME/KEY: misc_feature
<222> LOCATION: (34)..(38)
<223> OTHER INFORMATION: incomplete BglII restriction site, Plasmid

<400> SEQUENCE: 3

```
gggcgaattg gcggccgctc catgcaagcc taggatctcc ctcaagtagt aagcttgagt      60
attctatagt gtcacctaaa tagcttggcg taatcatggt catagctgtt tcctgtgtga     120
aattgttatc cgctcacaat tccacacaac atacgagccg gaagcataaa gtgtaaagcc     180
```

```
tggggtgcct aatgagtgag ctaactcaca ttaattgcgt tgcgctcact gcccgctttc    240
cagtcgggaa acctgtcgtg ccagctgcat taatgaatcg gccaacgcgc ggggagaggc    300
ggtttgcgta ttgggcgctc ttccgcttcc tcgctcactg actcgctgcg ctcggtcgtt    360
cggctgcggc gagcggtatc agctcactca aaggcggtaa tacggttatc cacagaatca    420
ggggataacg caggaaagaa catgtgagca aaaggccagc aaaaggccag gaaccgtaaa    480
aaggccgcgt tgctggcgtt tttccatagg ctccgccccc ctgacgagca tcacaaaaat    540
cgacgctcaa gtcagaggtg gcgaaacccg acaggactat aaagatacca ggcgtttccc    600
cctggaagct ccctcgtgcg ctctcctgtt ccgaccctgc cgcttaccgg atacctgtcc    660
gcctttctcc cttcgggaag cgtggcgctt tctcatagct cacgctgtag gtatctcagt    720
tcggtgtagg tcgttcgctc caagctgggc tgtgtgcacg aaccccccgt tcagcccgac    780
cgctgcgcct tatccggtaa ctatcgtctt gagtccaacc cggtaagaca cgacttatcg    840
ccactggcag cagccactgg taacaggatt agcagagcga gtatgtaggc ggtgctaca    900 gagttcttga agtggtggcc taactacggc tacactagaa gaacagtatt tggtatctgc    960
gctctgctga agccagttac cttcggaaaa agagttggta gctcttgatc cggcaaacaa   1020
accaccgctg gtagcggtgg tttttttgtt tgcaagcagc agattacgcg cagaaaaaaa   1080
ggatctcaag aagatccttt gatcttttct acggggtctg acgctcagtg gaacgaaaac   1140
tcacgttaag ggattttggt catgagatta tcaaaaagga tcttcaccta gatcctttta   1200
aattaaaaat gaagttttaa atcaatctaa agtatatatg agtaaacttg gtctgacagt   1260
taccaatgct taatcagtga ggcacctatc tcagcgatct gtctatttcg ttcatccata   1320
gttgcctgac tccccgtcgt gtagataact acgatacggg agggcttacc atctggcccc   1380
agtgctgcaa tgataccgcg agacccacgc tcaccggctc cagatttatc agcaataaac   1440
cagccagccg aagggccgag cgcagaagt ggtcctgcaa ctttatccgc ctccatccag   1500
tctattaatt gttgccggga agctagagta agtagttcgc cagttaatag tttgcgcaac   1560
gttgttgcca ttgctacagg catcgtggtg tcacgctcgt cgtttggtat ggcttcattc   1620
agctccggtt cccaacgatc aaggcgagtt acatgatccc cctgttgtgc aaaaaagcgg   1680
ttagctcctt cggtcctccg atcgttgtca gaagtaagtt ggccgcagtg ttatcactca   1740
tggttatggc agcactgcat aattctctta ctgtcatgcc atccgtaaga tgcttttctg   1800
tgactggtga gtactcaacc aagtcattct gagaatagtg tatgcggcga ccgagttgct   1860
cttgcccggc gtcaatacgg gataataccg cgccacatag cagaacttta aaagtgctca   1920
tcattggaaa acgttcttcg ggcgaaaac tctcaaggat cttaccgctg ttgagatcca   1980
gttcgatgta acccactcgt gcacccaact gatcttcagc atcttttact ttcaccagcg   2040
tttctgggtg agcaaaaaca ggaaggcaaa atgccgcaaa aaagggaata agggcgacac   2100
ggaaatgttg aatactcata ctcttccttt tcaatatta ttgaagcatt tatcagggtt   2160
attgtctcat gagcggatac atatttgaat gtatttagaa aaataaacaa ataggggttc   2220
cgcgcacatt tccccgaaaa gtgccacctg acgtctaaga aaccattatt atcatgacat   2280
taacctataa aaataggcgt atcacgaggc cctttcgtct cgcgcgtttc ggtgatgacg   2340
gtgaaaacct ctgacacatg cagctcccgg agacggtcac agcttgtctg taagcggatg   2400
ccgggagcag acaagcccgt cagggcgcgt cagcgggtgt tggcgggtgt cggggctggc   2460
ttaactatgc ggcatcagag cagattgtac tgagagtgca ccatatgcgg tgtgaaatac   2520
```

```
cgcacagatg cgtaaggaga aaataccgca tcaggaaatt gtaagcgtta atattttgtt    2580
aaaattcgcg ttaaattttt gttaaatcag ctcattttt  aaccaatagg ccgaaatcgg    2640
caaaatccct tataaatcaa aagaatagac cgagataggg ttgagtgttg ttccagtttg    2700
gaacaagagt ccactattaa agaacgtgga ctccaacgtc aaagggcgaa aaaccgtcta    2760
tcagggcgat ggcccactac gtgaaccatc accctaatca agttttttgg ggtcgaggtg    2820
ccgtaaagca ctaaatcgga accctaaagg gagcccccga tttagagctt gacggggaaa    2880
gccggcgaac gtggcgagaa aggaagggaa gaaagcgaaa ggagcgggcg ctagggcgct    2940
ggcaagtgta gcggtcacgc tgcgcgtaac caccacaccc gccgcgctta atgcgccgct    3000
acagggcgcg tccattcgcc attcaggctg cgcaactgtt gggaagggcg atcggtgcgg    3060
gcctcttcgc tattacgcca gctggcgaaa ggggatgtg  ctgcaaggcg attaagttgg    3120
gtaacgccag ggttttccca gtcacgacgt tgtaaaacga cggccagtga attgtaaatac   3180 gactcactat a                                                         3191
```

METHOD TO DETERMINE DNA MISMATCH REPAIR FUNCTION

This is a National Phase Application filed under 35 U.S.C. § 371 as a national stage of PCT/EP2012/062708 filed Jun. 29, 2012, claiming the benefit under 35 U.S.C. § 119(e) to U.S. Provisional Application No. 61/503,735, filed Jul. 1, 2011, and claiming benefit under PCT Articles 4 and 8 to Finland Application No. 20115709.

FIELD OF THE INVENTION

This invention relates to cancer diagnostics and provides methods based on a DNA mismatch repair assay for determining whether a human subject has an impaired DNA mismatch repair function; and for identifying a mismatch repair gene having a defective function and thus an increased risk of developing hereditary cancers, especially colorectal cancer. The method also provides a novel method of diagnosing Lynch syndrome. The method is performed on a sample derived from normal tissue, such as fibroblasts.

The working leading to this invention has received funding from the European Union Seventh Framework Programme (FP7/2007-2013) under grant agreement No. 232635.

The Sequence Listing submitted in text format (.txt) on Mar. 4, 2014, named "2110963US_SeqListingRevised", (created on Feb. 26, 2014, 13.1 KB), is incorporated herein by reference.

BACKGROUND OF THE INVENTION

Colorectal cancer (CRC) is the second most common cause of cancer-related death in the USA and Europe. According to a recent review article by Pino, M. S. and Chung, D. D. in Expert Rev Mol Diagn, 10(5):651-665, 2010, CRC is responsible for an estimated 52,000 deaths per year in the USA and 146,000 per year in the EU. Approximately 2-5% of newly diagnosed cases of CRC can be attributed to Lynch syndrome.

Lynch syndrome (LS), often also referred to as hereditary non-polyposis colorectal cancer syndrome (HNPCC), is manifested by early-onset colorectal and endometrial cancer, and an increased risk of certain extracolonic cancers, including tumors elsewhere in the gastrointestinal tract (e.g., stomach, small bowel, biliary tract), urinary collecting system (renal pelvis, ureter) and the female reproductive system (ovaries).

Studies of selected LS families have estimated a 70-80% lifetime risk of colon cancer with a mean age at diagnosis in the mid-40 s. The second most common cancer in LS is endometrial cancer, and women with LS have a cumulative lifetime risk of developing endometrial and ovarian cancer, with a mean age at diagnosis approximately 10 years earlier than sporadic cases. The lifetime risk for gastric cancer in LS patients varies between populations, with a particularly high incidence in areas such as China and Korea, where there is a high endemic risk of gastric cancer, with a lifetime risk of approximately 30%. In these areas, the risk for gastric cancer exceeds that for endometrial cancer.

Lynch syndrome is highly associated with autosomal dominant inheritance of mutations in genes fundamental to the DNA mismatch repair (MMR) mechanism, and it is caused by germline mutations in one of four DNA mismatch repair (MMR) genes, MLH1, MSH2, MSH6 and PMS2. Moreover, 25% of sporadic colon tumours, as well as a number of tumours of endometrium, ovary and some other organs and tissues, are deficient in MMR. MMR proteins normally recognize and repair mismatched nucleotides and insertion/deletion loops caused by the slippage of DNA polymerase during replication of short repeat sequences known as microsatellites.

The five proteins involved in the human mismatch repair (MMR) mechanism to maintain genomic integrity function as heterodimers are MutLα (MLH1+PMS2), MutSα (MSH2+MSH6) and MutSβ (MSH2+MSH3). MMR proteins correct base/base mismatches and small insertion/deletion loops (IDLs) that arise on the newly synthesised strand during DNA replication and recombination.

The most frequently affected genes include MLH1, MSH2, MSH6 and PMS2, whose germline variations are reported in the LOVD database (www.insight-group.org/; www.lovd.nl/). Although, the majority of mutations affecting MMR genes are truncating, a significant proportion of mutations result in a single amino acid substitution or an in-frame deletion and are difficult to distinguish from harmless polymorphisms. Such alterations are often referred to as variants of uncertain significance (VUS) due to the uncharacterized effect of the variation on the function of the polypeptide.

MMR-deficient tumours are strongly associated with microsatellite instability (MSI). However, the degree and type of MSI differ depending on the MMR gene affected (Kantelinen et al., British J Cancer, 1-6, 2010).

The mean age of cancer onset in LS is significantly lower than that of sporadic colorectal cancer based on the fact that in LS, an individual has already inherited susceptibility through a mutated allele and only needs a second hit in a somatic cell to lose MMR activity and start tumorigenesis. Hence, LS tumors are characterized by the lack or lowered level of a causative MMR protein as well as impaired DNA repair causing MSI.

The timely recognition of LS is essential to identify patients at high-risk who will require intensive cancer surveillance. Colonoscopy screening and removal of precursor lesions, adenomas, significantly reduces cancer morbidity and mortality in MMR gene mutation carriers (Jarvinen et al., Gastroenterology 118: 829-834, 2000). Analyses of cost-effectiveness indicate that colorectal cancer surveillance in MMR gene mutation carriers is effective and considerably less costly than the consequences of no surveillance. The Centers for Disease Control and Prevention (CDC) in the United States recommends that all individuals with a new diagnosis of colorectal cancer, regardless of age or family history, should be offered genetic testing for Lynch syndrome. The CDC report further states that there is currently not enough evidence to recommend any specific screening strategy vs. alternative strategies.

However, the wide variety of clinical phenotypes complicates LS diagnostics and several clinical guidelines have been established to distinguish LS families from the general CRC burden. Currently, the clinical diagnosis of LS greatly relies on the Amsterdam criteria or the revised Bethesda guidelines, which take into account the age of cancer onset, the number and segregation of affected individuals in a family, and the level of MSI (Pino & Chung, Supra). However, many putative LS families do not fit these criteria and could be recognised as LS families only by characterizing a pathogenic germline MMR gene mutation in them.

The traditional diagnostic workflow to identify MMR gene mutation carriers, i.e., subjects afflicted by Lynch syndrome, involves several phases, such as tumor studies, DNA analyses, in vitro tests for mutation pathogenicity and proceeds from detecting a genetic defect to evaluating if it is associated with reduced MMR capacity. The first clinical step in diagnosing LS associated tumors includes immunohistochemistry (IHC) and MSI analysis followed by mutation screening dictated by the IHC and MSI results. One strategy for screening mutations is analyzing all four MMR genes (MLH1, MSH2, MSH6 and PMS2). When a pathogenic mutation is found, LS can be confirmed or in the absence of a MMR gene variation, considered unlikely but not ruled out (since no method, whether used alone or in combination, is 100% sensitive and specific).

A recent publication by the present inventors (Kansikas et al., Hum Mutat 32:107-115, 2011) discloses that testing in vitro synthesized mutant proteins for MMR capacity forms the cornerstone for pathogenicity testing. The published in vitro MMR assay studies the phenotypic consequences of LS mutations in a homologous human MMR system. Construction of the LS mutant protein requires that the genetic defect in question is found and fully characterized on DNA sequence level. A three-step decision tree was thus proposed (Couch et al., Hum Mutat 29:1314-1326, 2008):

However, there are several disadvantages associated with the present tests used for the establishment of a clinical diagnosis:

MSI testing is labour-intensive and requires expert molecular pathologic services, and while it is a hallmark for LS, it is not specific for it. Approximately 10-25% of sporadic CRCs and many extracolonic cancers also exhibit MSI. Furthermore LS-associated and sporadic MSI-positive CRCs have many histopathologic features in common, but differ in that sporadic MSI CRCs are not associated with a positive family history.

An inherent potential shortcoming of the IHC test is that the technique is somewhat subjective and depends upon the quality of tissue preparation, staining and interpretation of the results. Interestingly, abnormal staining patterns may be due to tissue preservation and the tumor microenvironment. For example, tissue hypoxia or oxidative stress may diminish the function of MMR proteins, even in genetically MMR-proficient tissues, leading to a focal loss or weak staining. Secondary abnormalities in MMR genes may also lead to rare staining patterns.

However, the most obvious limitation related to present methods of diagnosing LS, is that the tests are based on genetic testing and mutation analysis on subjects from a family with a known, or suspected, LS history, or on subjects already affected by cancer. This fact does not make present diagnostic methods suitable for routine screening of healthy subjects suspected of being carriers. Furthermore, the present testing schemes are very laborious requiring well-equipped laboratories as well as highly skilled laboratory personnel. It has been estimated that the steps including IHC, MSI and mutation analysis amount to about 3500 € per test, which is expensive for a routine test.

There is thus a well-established and recognized need for accurate, simpler, but cheaper and clinically suitable tests for identifying, whether a person is a carrier of MMR gene mutations related to Lynch syndrome and thus subjected to a high risk of colorectal cancer, as well as other cancers.

BRIEF DESCRIPTION OF THE INVENTION

The object of the present invention is to provide novel methods and means for achieving accurate, simple, cheap and clinically suitable tests for detecting decrease in MMR efficiency without preliminary knowledge of LS history or cancers in subjects, and thus solving the problems of current methods of diagnostics. The present invention relates to a quantitative method for determining whether a human subject has an impaired DNA mismatch repair function, wherein said method comprises a) producing a nuclear extract from a sample obtained from said human subject, b) providing MMR proficient and MMR deficient nuclear protein extracts as positive and negative controls, respectively, c) combining in separate vials each nuclear extract with at least one mismatch-bearing heteroduplex DNA substrate, d) performing a mismatch repair assay on said sample and control nuclear protein extracts and said substrate, and e) determining whether said sample nuclear extract is capable of repairing said substrate DNA molecule. Preferably said sample comprises normal cells obtained from a constitutive tissue, more preferably fibroblast cells or blood-derived cells.

In one embodiment of the invention, said substrate is derived from a plasmid having SEQ ID NO:1, and preferably said substrate further comprises a nucleic acid sequence selected from the group consisting of SEQ ID NO:2 and SEQ ID NO:3.

In another embodiment the MMR deficient nuclear extract is derived from a cell line selected from the group consisting of HCT116 and LoVo cells. In a specific embodiment the total amount of nuclear extract per vial is in the range of 50-500 µg, preferably 50-200 µg, more preferably 75-100 µg.

The present invention further relates to a quantitative method for identifying a mismatch repair gene having a defective function, wherein said method comprises a) producing a nuclear protein extract from a sample obtained from a human subject, b) providing MMR proficient and MMR deficient nuclear protein extracts as positive and negative controls, respectively, c) mixing at least one MMR deficient nuclear protein extract with said sample extract, d) combining in separate vials each nuclear extract provided in steps a-c with at least one mismatch-bearing heteroduplex DNA substrate, e) performing a mismatch repair assay on said nuclear extracts and said substrate, and f) identifying said defective gene by determining whether said sample nuclear extract is capable of repairing said substrate and complementing said MMR deficient nuclear extract. Preferably said sample comprises normal cells obtained from a constitutive tissue, more preferably fibroblast cells or blood-derived cells.

In one embodiment of the invention, said substrate is derived from a plasmid having SEQ ID NO:1, and preferably said substrate further comprises a nucleic acid sequence selected from the group consisting of SEQ ID NO:2 and SEQ ID NO:3.

In another embodiment the MMR deficient nuclear extract is derived from a cell line selected from the group consisting of HCT116 and LoVo cells. In a specific embodiment the total amount of nuclear extract per vial is in the range of 50-200 µg, preferably 75-100 µg.

Furthermore, the present invention relates to a novel method for diagnosing Lynch syndrome in a human, based on the identification of a defective DNA mismatch repair gene using an MMR assay according to the present invention, from a clinical sample obtained from a constitutive tissue of a human subject.

The present invention also relates to a kit for use the methods according to the present invention, comprising at least one mismatch-bearing heteroduplex DNA substrate, at least one MMR deficient nuclear extracts, and an MMR proficient nuclear extract as a positive control. Preferably said MMR deficient nuclear extracts are derived from a cell line having an MMR deficiency in respect of either MLH1, MSH2 or MSH6, preferably from HCT116 or LoVo cells.

In a specific embodiment of the present invention, the kit comprises at least two MMR deficient nuclear extracts.

In a further embodiment the kit may also include additional reagents necessary for performing the MMR assay, such as 10×MMR buffer comprising 200 mM Tris-HCL pH 7.6, 400 mM KCl, 50 mM MgCl2, 10 mM Glutathione, BSA 500 µg/ml, 1 mM each dNTP and 15 mM ATP; and a STOP solution for MMR assay comprising 42 mM EDTA, 1.2% SDS, 50.4 µg/ml Proteinase K. Optionally, the kit may comprise reagents for clarifying the sample, such as TE buffer, phenol/chloroform/isoamyl alcohol and chloroform; for precipitating said sample, such as NaCl and ethanol; and for detecting the repair, such as RNase A and restriction enzymes BglII and Eco31I with buffer and loading dye.

BRIEF DESCRIPTION OF THE FIGURES

In the following the invention will be described in greater detail by means of preferred embodiments with reference to the attached drawings, in which.

DETAILED DESCRIPTION OF THE INVENTION

Figure 1:
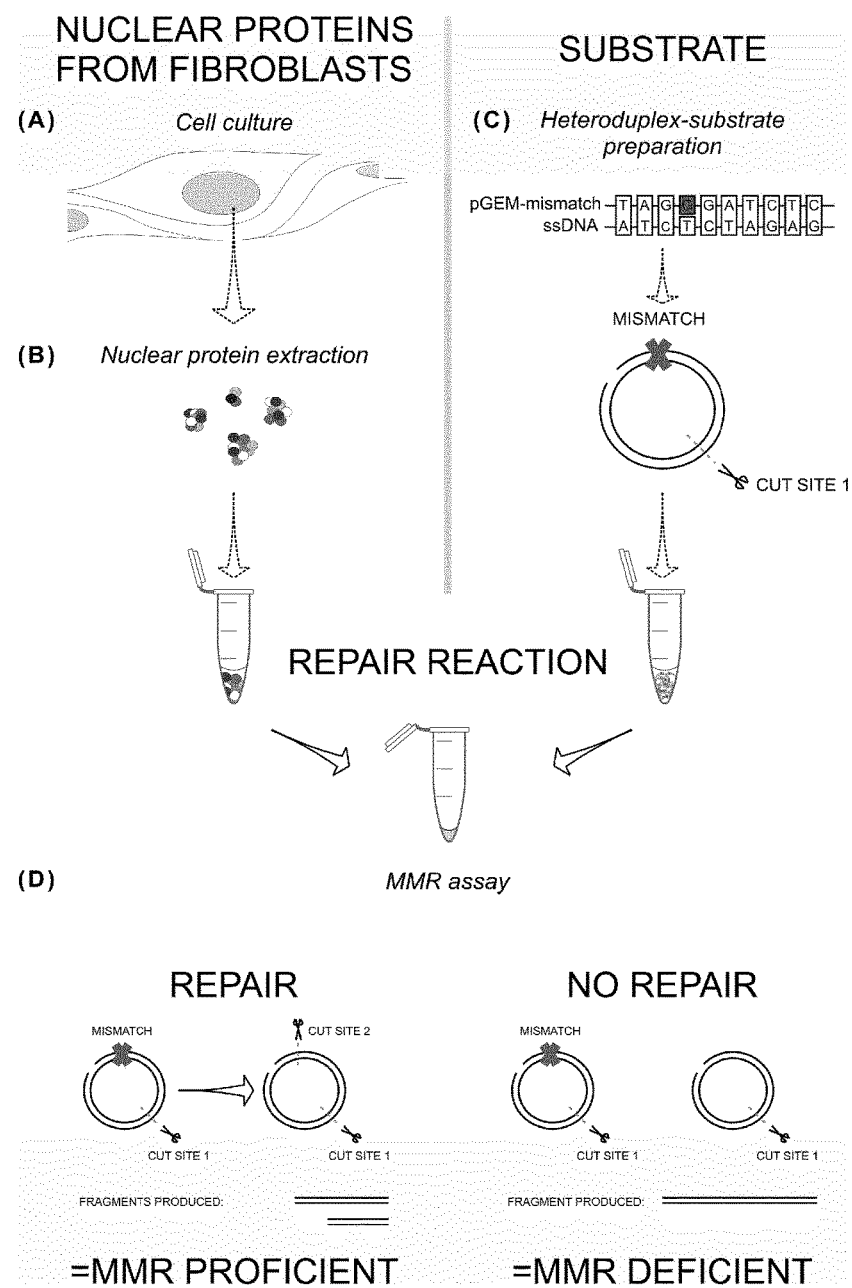
FIG. 1 is an overview of the instant method, comprising (FIG. 1(A) culturing the primary cells from a normal constitutive tissue sample of the human subject, (FIG. 1(B) producing a nuclear protein extract from the cultured primary fibroblast cells, (FIG. 1(C) preparing at least one mismatch-bearing heteroduplex DNA substrate and combining in separate vials the primary fibroblast cell nuclear protein extract with the substrate, FIG. 1(D) performing a mismatch repair assay on the primary fibroblast cell nuclear protein extract with the substrate, resulting in repaired homoduplex and/or unrepaired heteroduplex substrate DNA molecules.

It has now surprisingly been found, that a functional assessment of DNA mismatch repair (MMR) efficiency can be used to recognize individuals with an inherited MMR deficiency, and thus at notable risk to develop cancer. The present invention provides a novel MMR assay, which is aimed at identifying deficient ability for MMR (FIG. 1). The assay according to the present invention is applicable without any prior knowledge of the underlying MMR gene sequence or regulatory change, family history, cancer history or IHC results and therefore constitutes a novel approach for diagnostic purposes. The assay is ideal for screening purposes of MMR mutation carriers in large populations, and thus for finding persons with high risk for cancer development.

The present invention relates to a simple test protocol consisting of only one assay, whereas the traditional diagnostic workflow to identify MMR gene (Lynch syndrome) mutation carriers involves several tests, and proceeds from detecting a genetic defect to evaluating if it is associated with reduced MMR capacity. The present invention provides a one-step procedure that evaluates whether or not an individual carries a MMR defect in the germline, determined by a quantitative MMR assay. The method according to the present invention is based on detection of decreased MMR capacity in a normal tissue sample, such as blood, mucosa or fibroblasts, preferably fibroblasts or lymphoblasts obtained from the subject to be tested.

As used herein, the term "normal" tissue is intended to include any healthy, non-malignant tissue, preferably a constitutive tissue.

As used herein, the term "constitutive tissue" refers to tissues of non-malignant cells which substantially represent the genetic composition inherited at birth and which may be derived from any part of the human body accessible to sampling, e.g. mucosa or fibroblasts.

The test protocol of the present invention relates to a quantitative method. As used herein, the term "quantitative method" refers to a method, which gives results of MMR efficiency with varying intensity, i.e. it is not an on/off test. The present MMR assay detects deficiencies of MMR proteins as a decrease in repair efficiency (see FIG. 4 for MLH1 and MSH2). As used herein, MMR genes or proteins refer to any genes or proteins participating in the MMR process, for example selected from the group consisting of MLH1, MSH2, MSH6, MLH3, MSH3, PMS1, PMS2 and EXO1. In a specific embodiment, deficiencies of MMR proteins MLH1, MSH2 and/or MSH6 are detected by the method or means of the present invention. Indeed, there is still some ability to correct mismatches, if for example only one normal MMR allele is present, as is the case in normal cells of all MMR gene mutation carriers in LS families, or if a MMR gene is partly inactivated. In comparison, tests of prior art used for cancer cells reveal whether MMR occurs (both wild type alleles present) or is absent (both wild type alleles absent) representing an on/off test for MMR.

MMR of the DNA takes place in the nucleus of the cell, and only the MMR proteins of the nucleus take part in the repair process. By the method of the present invention it is possible to assay the functionality of those MMR proteins which have headed to the nucleus for repair activity in vivo, because a starting material of the method is a nuclear extract. On the contrary, in the traditional workflow, the MMR assay is used for studying MMR efficiency of the mutated MMR protein products constructed in vitro. In these in vitro tests, the proteins to be tested are artificially added to the nuclear extract without the possibility to study only the proteins naturally present in nuclei. Thus, the pathogenicity test of the present invention differs from functional tests of the prior art by revealing the actual MMR ability of the nucleus. And therefore, by the method of the present invention, it is also possible to find out problems of nuclear localization of the MMR proteins.

The methods of the prior art utilize cell extracts i.e. cytoplasmic extracts (CE) instead of nuclear extracts. Tests with cytoplasmic extracts give wrong information of amounts and proportions of MMR proteins, which are capable for repair processes in reality. Therefore, tests with cytoplasmic extracts are suitable only for on/off test and not for quantitative testing of MMR.

In the methods of the present invention, MMR ability is detected directly from the agarose gel without using any indirect detection method of the prior art such as complementation assays in *E. coli*, wherein detection is arranged by expression of lacZα.

The one-step assay according to the present invention may, optionally, be followed by or include steps for identifying an underlying genetically or epigenetically defected gene if one so wishes, but this is not necessary for a clinical diagnosis. Contrary to traditional tests, the method according to the present invention allows for the recognition of individuals with increased cancer susceptibility due to deficient MMR even in cases where no family member has, yet, developed cancer, where mutation tests result in no detectable change, and/or where the underlying change is not genetic but epigenetic (regulatory).

The basic principle, as well as different embodiments of the proposed assay is shown in an array format in Table 1, wherein Y denotes an MMR deficient nuclear protein extract, X a test sample nuclear protein extract and Z an MMR proficient positive control nuclear protein extract.

TABLE 1

| MMR+/− | MMR gene 1+/− | MMR gene 2+/− | MMR gene 3+/− |
|---|---|---|---|
| Y | $Y_1$ | $Y_2$ | $Y_3$ |
| X | $X + Y_1$ | $X + Y_2$ | $X + Y_3$ |
| Z | Z | Z | Z |

In one embodiment of the present invention a test sample nuclear protein extract (X) is prepared from cultured normal cells, such as fibroblasts, obtained from the subject to be tested, and an MMR assay according to the present invention is performed in vials comprising Y (MMR deficient nuclear extract), X and Z (MMR proficient positive control nuclear extract), respectively. The repair reaction converts heteroduplexes not susceptible to cleavage by the restriction endonuclease to homoduplexes, which can be cleaved. If sample X is MMR proficient, the substrate heteroduplex will thus be cleaved and linearized into three fragments, whereas only one fragment will result because of linearization, if X is MMR deficient. Correspondingly, Y will produce only one fragment, whereas Z will produce three. This embodiment of the present invention, the MMR+/− assay (+/− indicating that one allele of the MMR gene is functioning and the other one is deficient), will allow determination of whether the human subject tested has an impaired/deficient MMR function or a normal MMR function.

In another embodiment of the present invention, the sample nuclear extract (X) is used to complement an MMR deficient nuclear extract (Y) to form X+Y. The complemented test samples (X+Y), as well as the positive (Z) and negative (Y) controls, are then used in an MMR assay according to the present invention to study the ability to repair mismatches. The repair efficiency is quantified by measuring the cleavage efficiency using the repair efficiency of the proficient fibroblast nuclear extract (Z) as a reference level, as exemplified in example 8 and FIG. 4.

The number of MMR deficient nuclear extracts ($Y_n$) included in the assay may be varied depending on if a defective (s) are considered important to identify. In one preferred embodiment of the method according to the present invention $Y_1$ is MLH1 deficient and $Y_2$ is MSH2/MSH6 deficient. In a further embodiment of the present invention $Y_3$ could be PMS2 deficient. However, any one of said MMR deficient nuclear extracts ($Y_n$) could be omitted or added and used, in any combination. A person skilled in the art would be able to construct a test panel suitable for the clinical situation in question.

A typical diagnostic assay according to the present invention is performed as described in more detail below.

A. Tissue Samples

The tissue sample to be tested may be any normal tissue, which is easily obtained and processed. In one specific embodiment of the present invention, the tissue sample of choice is a human skin punch or excision biopsy, which may have been obtained by any method well known to a person skilled in medical care.

Other tissue samples, which may be used in a method according to the present invention, include blood samples, and mucosal swabs.

B. Expansion of the Sample Cells

In order to examine the mismatch repair (MMR) ability of the cells, a sufficient amount of cells have to be grown prior to extracting nuclear proteins from them. Cells are grown in standard cell culture conditions, suitable for the type of cells used and well known in the art, and thereafter collected by gently spinning them down.

Any cell type derived from a clinical sample taken from a human subject, including malignant cells derived from a tumor, may be used in a method according to the present invention. Preferred cell types for use in a test according to the present invention are human fibroblasts. Another preferred cell type is blood-derived human cells, such as lymphoid cells.

Most preferably, cells for the test of the present invention are normal primary cells or transformed normal cells.

C. Extraction of Nuclear Proteins from Human Fibroblast Cells

MMR proteins are extracted from the nuclei of the cells. Cells are spun down, counted and washed with saline buffer in order to remove any remaining trypsin. The cells are further washed with isotonic buffer before they are spun down and swollen with the osmotic effect of a subsequent hypotonic wash. A narrow needle is used to disrupt the cell membranes until the majority of the cells are confirmed to have lysed under the microscope.

After spinning the cells down, the supernatant containing the cytoplasmic fraction is removed. The nuclear proteins are extracted from the remaining nuclear fraction by incubation in cold extraction buffer with salt after which any remaining nuclear debris is spun down and removed as the remaining pellet. The extracted nuclear protein sample is thereafter dialysed in the presence of proteinase inhibitors, and further cleared by centrifugation prior to storing in −80° C. The protein content of the samples is quantified by a fluorometer.

D. Substrate Preparation

A circular heteroduplex plasmid substrate for use in the MMR assay according to the present invention is made by reannealing a single stranded DNA (ssDNA) and a denatured matching plasmid DNA with one non-homologue site.

The ssDNA is produced from a plasmid with the help of bacterial cells and a commercially available helper phage under heavy antibiotic selection. Cell debris is spun down and phage particles are collected by precipitation and further centrifugation. Bacterial cells are also removed by centrifugation and any remaining chromosomal DNA originating from the bacteria is removed with enzymatic treatments. Upon clearing of the sample, the ssDNA is released from the phage capsid proteins with the help of a proteinase-enzyme.

A double stranded (ds) plasmid template containing the mismatch error is amplified in and purified from bacterial cells. In order to have a 5' nick upstream of the site of the error, a specific restriction enzyme is used to linearize the construct after which the sample is precipitated and dissolved in an appropriate volume of buffer.

In order to make the mismatch-bearing heteroduplex substrate for the MMR assay according to the present invention, the ssDNA and the matching plasmid DNA described above are denatured and reannealed together. Subsequent washing steps, including the removal of salts and unhybridized linear dsDNA as well as unhybridized ssDNA followed by ethanol precipitation ensure the purity of the final product. The concentration is measured with a spectrophotometer as well as by gel electrophoresis which also serves to verify the purity of the sample.

E. The MMR Assay According to the Present Invention

An MMR assay according to the present invention may be used only for determining whether the MMR function of the test sample is deficient or not, but can also distinguish between MMR capability of nuclear proteins extracted from cells with deficient MMR and of those extracted from MMR proficient cells, as described above. To identify a MMR deficient gene, the sample nuclear extracts (X) are used to complement separately MLH1 ($Y_1$) and MSH2/MSH6 ($Y_2$) deficient nuclear extracts.

An MMR assay according to the present invention is carried out by combining about 50-500 µg, preferably about 50-200 µg, more preferably about 75-100 µg of nuclear protein extract with an excessive amount of circular plasmid substrate (heteroduplex), whereas in the case of complementing a well characterised MMR deficient cell line to determine the MMR gene causing the deficiency, the total amount of the two extracts used in the assay should not exceed that of 200 µg. The repair reaction is induced in the presence of an MMR buffer which ensures optimal salt concentration whilst also providing ATP and deoxyribonucleotides. The repair reaction is terminated enzymatically and the proteins are removed from the sample by a phenol/chloroform/isoamyl alcohol extraction.

After precipitation, the sample is subjected to a double digestion, which cleaves the substrate heteroduplex DNA into two smaller fragments if the repair process was successful. These two smaller fragments are visualized by agarose gel electrophoresis. As the substrate DNA is added in excess, a linearized full length product will also always be visible. Where no repair has occurred, only the full length linearized plasmid DNA will be apparent.

It is a further object of the present invention to provide a kit comprising the necessary reagents for performing a method according to the present invention. A kit according to the present invention includes standard reagents, such as a substrate comprising necessary mismatch bearing heteroduplex DNA substrate(s); at least one, but preferably two, MMR deficient nuclear extract(s); and an MMR proficient nuclear extract as a positive control. In a specific embodiment of the present invention, said MMR deficient nuclear extracts are derived from cell lines deficient for MLH1 and MSH2/MSH6, respectively. More specifically, said MMR deficient nuclear extracts are derived from HCT116 and LoVo cells.

The reagents included in a kit according to the present invention should be chosen according to the basic principle disclosed in Table 1. In one embodiment, a first nuclear extract (Y1) is deficient of MLH1, whereas a second nuclear extract (Y2) is deficient of MSH2/MSH6. If a tested sample does not complement said first nuclear extract, but does complement said second nuclear extract, said test sample reveals a MLH1 deficiency. However, if said tested sample does complement said first nuclear extract, but not said second nuclear extract, said test sample reveals that the tested subject has either an MSH2 or an MSH6 deficiency.

Optionally, a kit according to the present invention may include further MMR deficient nuclear extracts, which specifically distinguish between deficiencies in the MSH2 and MSH6 genes. Such nuclear extracts may be derived from cell lines, such as MSH6 deficient HCT-15/DLD-1 (ATCC CCL-225/221).

Optionally, a kit according to the present invention may also comprise additional reagents necessary for performing the MMR assay, such as necessary buffers and nucleotides.

One example of a kit according to the present invention is given in the examples below.

EXAMPLES

The following examples are given to further illustrate embodiments of the present invention, but are not intended to limit the scope of the invention. It will be obvious to a person skilled in the art, as technology advances, that the inventive concept can be implemented in various ways. The invention and its embodiments are thus not limited to the examples described herein, but may vary within the scope of the claims.

Example 1. Culturing Fibroblasts Taken from the Subject to be Tested

Fibroblast cells are grown in Dulbecco's Modified Eagle Medium (Invitrogen, CAT #31966-021) in a 37° C. 5% $CO_2$ incubator. The growth medium is supplemented with 10% fetal bovine serum (Invitrogen, CAT #10106-169), 2× Non Essential Amino Acids (Invitrogen, CAT #10370-070) and 2% Penicillin-Streptomycin (Invitrogen, CAT #15070-063). The cells are subcultured 1:2-1:6 when approximately 80-90% confluent with the help of Trypsin 0.25% EDTA (Invitrogen, CAT #25200-072). To maintain the silencing in the MLH1-depleted derivative cell line FB-M1 or MSH2-depleted derivative cell line FB-SH13, 150 µg/µl hygromycin B (Invitrogen, CAT #10687-010) is added to the growth medium. Cells are grown in cell culture treated filter-capped 175 bottles (NUNC, CAT #145-178883) until approximately $5 \times 10^8$-$10^9$ cells are gathered for the extraction of nuclear proteins.

Example 2. Cell Lines and Nuclear Extracts

Adherent human cancer cell lines HeLa, LoVo and HCT116 (American Type Culture Collection, Manassas, Va., USA) are cultured according to instructions of manufacturers. HeLa cells (ATCC CCL-2) are MMR proficient epithelial cells derived from the cervix of a female individual, whereas HCT116 (ATCC CCL-247) and LoVo cells (ATCC CCL-229) are MMR deficient epithelial cells derived from the colon of a male individual. HCT116 cells lack MLH1 whereas in LoVo cells, the MSH2 gene is inactivated causing a deficiency of MSH2, MSH3 and MSH6 proteins. The lack of MSH2 has been associated with the proteolytic degradation of its counterparts MSH3 and MSH6.

HeLa cells are grown in DMEM medium complemented with 2% L-glutamine, 10% FBS and 5% PS. LoVo cells are grown in F12 (or F12:DMEM) medium (Invitrogen, CAT #31765-027/31331-028) complemented with 2% L-glutamine, 10-20% FBS and 5% PS whereas HCT116 cells are grown in McCoys 5A medium (Invitrogen, CAT #22330-021) complemented with 2% L-glutamine, 10% FBS and 5% PS.

The FB-M1 cell line was produced as described in McDaid et al, BJC, 101:441-451, 2009. In brief, overlapping oligonucleotides producing siR-NA targeting MLH1 were designed and ligated into a commercially available shRNA vector pSilencer™ (Ambion CAT #AM7209). The construct was verified by sequencing before linearising and electroporating $1 \times 10^7$ cells with 1 µg DNA. Serum enriched medium was immediately added and the cells were plated a $5 \times 10^5$ before adding hygromycin selection (150 µg/µl) for 10-14 days. Similarly, the FB-SH13 cell line was produced using overlapping oligonucleotides producing siRNA targeting MSH2 into the pSilencer™ shRNA vector.

Correspondingly, fibroblast cell lines comprising other MMR gene-mutations, such as silenced MSH6 may be prepared, using shRNA vector pSilencer™ 4.1—CMV Hygro (Cat#AM5777). The fibroblast nuclear extracts were prepared according to the following protocol (Lahue et al, Science, 245:160-164, 1989):
1. Harvest $5 \times 10^8$-$10^9$ log phase cells with trypsin.
2. Count the cells.
3. Centrifuge at 500×g for 10 min +4° C.
4. Resuspend the cell pellet in 20-30 ml of cold 1× isotonic buffer (20 mM Hepes pH 7.5, 5 mM KCl, 1.5 mM MgCl, 250 mM sucrose, 0.2 mM PMSF, 1× complete EDTA-free protease inhibitor mixture (Roche Diagnostics GmbH, Mannheim, Germany), 0.25 µg ml-1 aprotinin, 0.7 µg ml-1 pepstatin, 0.5 µg ml-1 leupeptin, 1 mM DTT) and centrifuge as before.
5. Estimate the packed cell volume and resuspend it in 20-30 ml cold 1× hypotonic buffer (isotonic buffer without sucrose) and centrifuge immediately as before.
6. Remove the supernatant and resuspend the cell pellet in 1× cold hypotonic buffer to obtain a cell density of $1$-$2 \times 10^8$ cells/ml. The packed cell volume is substracted from the resuspension volume.
7. Disrupt cells by a syringe with a narrow gauge needle by drawing cells slowly into the syringe and then ejecting them with a single rapid stroke. Cell disruption is to be carried out until 80-90% of the cells have lysed, as verified with under the microscope (50 µl of 0.4% Trypan blue in PBS with 45 µl PBS and 5 µl cells).
8. Centrifuge the disrupted cells at 3000×g for 10 min +4° C. and remove the supernatant.
9. Estimate the nucleic pellet volume and add ⅓ to ⅕ of cold extraction buffer (25 mM Hepes pH 7.5, 10% sucrose, 1 mM PMSF, 0.5 mM DTT, 1 µg ml-1 leupeptin) to the volume of the pellet. Resuspend the pellet well by pipetting up and down.
10. Measure the new volume and add NaCl to a final concentration of 0.155 M whilst mixing.
11. Rotate the mixture for 60 min at 4° C.
12. Centrifuge at 14500×g for 20 min at 2° C.
13. Dialyse the sample for 2×50 min in a 3.500 MWCO cassette in 1 L of cold dialysis buffer (25 mM Hepes pH 7.5, 50 mM KCl, 0.1 mM EDTA pH 8, 10% sucrose, 1 mM PMSF, 2 mM DTT, 1 µg ml-1 leupeptine). Change the buffer after the first 50 minutes.
14. Clarify the extract by centrifugation at 20000×g for 15 min at 2° C.
15. Snap freeze nuclear proteins in liquid nitrogen and store at −80° C.

Example 3. Western Blot Analysis

Protein expression levels in the nuclear extracts (NEs) were studied by western blot analysis using 50 mg of NE and 0.1-5 µl of wild type total protein extract by means of sodium dodecyl sulphate polyacrylamide gel electrophoresis. The proteins were blotted into nitrocellulose membranes (Amersham Hypond™, PVDF, Amersham Pharmacia Biotech, Uppsala, Sweden), which were subsequently incubated with monoclonal antibodies anti-MSH2 (Calbiochem, San Diego, Calif., USA, MSH2-Ab1, NA-26, 0.2 mg/ml), anti-MSH3 (BD Transduction Laboratories, Lexington, Ky., USA, M94120, 250 mg/ml), anti-MSH6 (BD Transduction Laboratories, clone 44, 0.02 mg/ml), anti-PMS2 (Calbiochem/Oncogene Research, San Diego, Calif., USA, Ab-1, 0.2 mg/ml) and anti-MLH1 (BD Biosciences/Pharmingen, San Diego, Calif., USA, clone 168-15, 0.5 mg/ml). Ubiquitously expressed α-tubulin was used as a loading control to estimate the MMR protein levels in the extracts (anti-α-tubulin; Sigma, Louis, Mo., USA, DM1A, 0.2 mg/ml).

Example 4. Production of Wild-Type Heterodimer Protein Complexes

*Spodoptera frugiperda* (Sf9) (Invitrogen, Carlsbad, Calif., USA) insect cells were transfected with bacmid DNA carrying wild-type (WT) MSH2, MSH3, MSH6, PMS2 or MLH1 cDNA fragments afterwhich the cells were re-infected to obtain a higher yield of recombinant baculoviruses (Nyström-Lahti et al, 2002). These WT-recombinant baculoviruses were used to co-infect Sf9 cells for protein production forming the heterodimer complexes assayed: MutLα (MLH1+PMS2), MutSα (MSH2+MSH6) and MutSβ (MSH2+MSH3). The heterodimeric complexes were extracted as total protein extracts (TE) at 50 h (MutLα) or 72 h (MutSα and MutSβ) by lysing and centrifuging the cells down.

Example 5. Substrate Preparation

Preparation of Heteroduplex Molecules.

Figure 6:
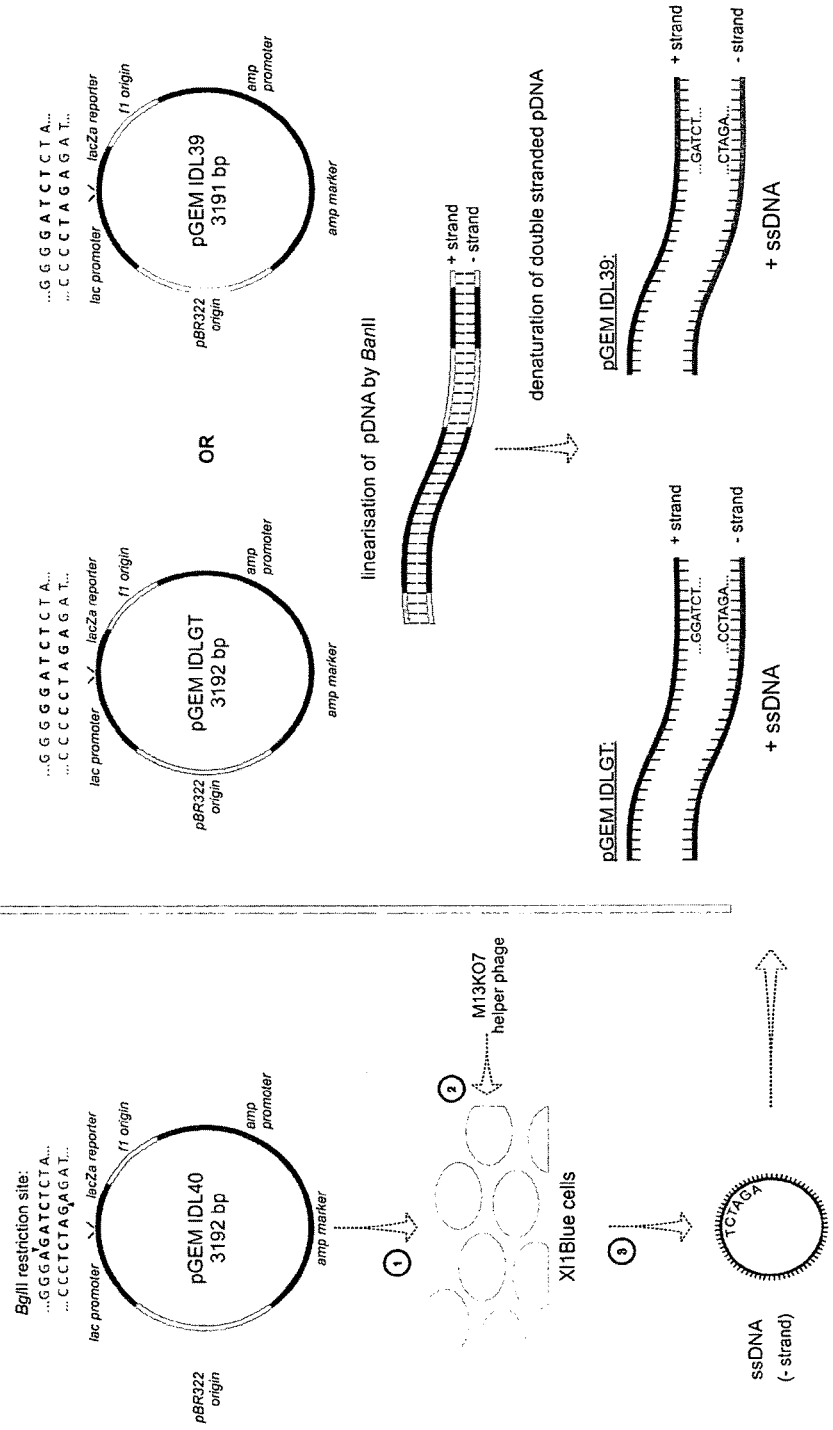
FIG. 6 is a schematic presentation of the substrate preparation, including the plasmid presentations of pGEM-IDL40 SEQ ID NO: 1, pGEM-IDLGT SEQ ID NO:2 and pGEM-IDL39 SEQ ID NO: 3, and their derivative constructs 5'IDLGT and 5'IDL1.
Figure 6:
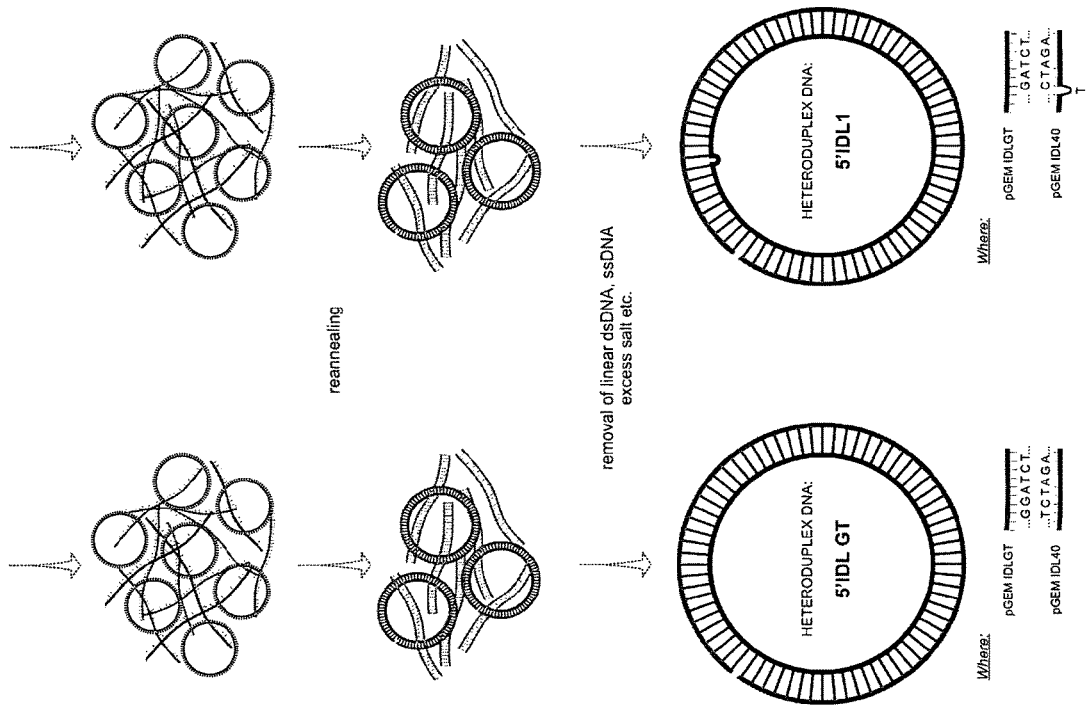
Figure 7:
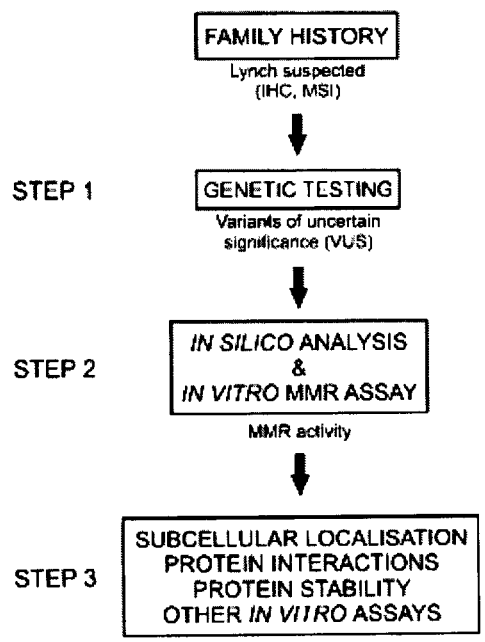
FIG. 7 is a schematic of the three-step decision tree for the construction of the LS mutant protein (Couch et al., Hum Mutat 29:1314-1326, 2008)

The heteroduplex DNA molecule is a circular 3192 bp long molecule with a single-strand nick 445 bp upstream from the site of the mismatch. This contains a complete BglII restriction site. The molecule is made by annealing single stranded DNA from a pGEM-IDL40 plasmid (FIG. 6) together with an error introducing plasmid based on the same construct (pGEM-IDL GT, for 5'GT substrate or pGEM-IDL-39 for 5'IDL1 substrate).

Single-stranded DNA (ssDNA) was prepared by infecting pGEM IDL40 trans-formed XL1-blue bacteria cells with the M13K07 bacteriophage (Amersham Biosciences, Piscataway, N.J., USA), which replicates the anti-sense strand that can thereafter be extracted from the cells. The lower (−) strand amplified by the M13 phage has the sequence depicted in SEQ ID NO: 1, where the BglII restriction site is annotated.

Two different heteroduplex constructs were prepared; a G-T mismatch (5'GT) and a single nucleotide 5'IDL1. Site-directed mutagenesis was carried out to a pGEM-IDL40 according to manufacturer's instructions (Quik-Change® Site-directed mutagenesis, Stratagene, La Jolla, Calif., USA) to produce the error containing pGEM IDLGT and pGEM IDL39 plasmids.

The 5'GT substrate was made by annealing the ssDNA with the mismatch containing pGEM-IDLGT. This 3192 bp long base plasmid (pGEM-IDLGT) for linear dsDNA contains an incomplete BglII restriction site (GGATCT). The upper (+) strand is complementary to ssDNA produced from IDL40, except for the G which is replacing the A that would be complementary in the BglII site. The sequence of the pGEM-IDLGT is depicted in SEQ ID NO: 2 and the incomplete BglII restriction site annotated.

The 5'IDL1 substrate was made by annealing the ssDNA with the error containing pGEM-IDL1. This 3191 bp long base plasmid (pGEM-IDL39) for linear dsDNA contains an incomplete BglII restriction site (−GATCT). Upper (+) strand is complementary to ssDNA produced from IDL40, except for delA in the BglII site. To create the 5' nick the circular substrate was linearized with BamII or DraIII before reannealing. The sequence of pGEM-IDL39 is depicted in SEQ ID NO: 3 and the incomplete BglII restriction site is annotated.

Example 6. MMR Assay According to the Present Invention

The present invention is a modification of the previously described in vitro MMR assay (Nyström-Lahti et al, 2002), allowing to assay the MMR capability directly of a nuclear extract. Furthermore, complementation can be used to characterise the defected MMR gene in the sample by complementing a characterised MMR deficient extract as described in Table 1. Repair reactions are standardised to include a total of 75-100 µg of NE. The excess amount of the heteroduplex DNA substrate (5'GT or 5'IDL1) is set to 100 ng. The repair reaction is performed in 20 µl volume with the following reagents:
100 ng heteroduplex substrate
75-100 µg nuclear extract
2 µl of 10×MMR buffer (200 mM Tris-HCL pH 7.6, 400 mM KCl, 50 mM MgCl2, 10 mM Glutathione, BSA 500 µg/ml, 1 mM each dNTP, 15 mM ATP)
KCl to get 110 mM final concentration
add $H_2O$ up to 20 µl.

As the reaction is to be done in the total volume of 20 µl and a final KCl concentration of 110 mM, the KCl content of the nuclear extract needs to be taken into consideration (2 µl of 10×MMR buffer brings KCl content of the reaction mix to 40 mM). The KCl content of nuclear extract is assumed to be 75 mM/µl.

The typical protocol of the MMR assay according to the present invention is:
1. Pipette the components of the repair reaction together on ice and incubate 30 min at 37° C.
2. Stop the reaction by adding 30 µl of fresh stop solution (42 mM EDTA, 1.2% SDS, 50.4 µg/ml Proteinase K). Incubate at 37° C. for 20 min.
3. Add 1 volume (50 µl) of TE buffer pH 8.0.
4. Add 1 volume of phenol-chlorophorm-isoamylic alcohol (25:24:1) and vortex for 10 s. Centrifuge at maximum speed for 10 min at room temperature.
5. Transfer the upper phase (approximately 90 µl) to a new tube and add an equal volume of chloroform. Vortex for 10 s and centrifuge at maximum speed for 10 min at room temperature.
6. Transfer 85 µl of the upper phase to a fresh tube for ethanol precipitation.
7. Add NaCl to obtain a final concentration of 150 mM followed by 2.5 volumes of cold absolute ethanol. Incubate at −20° C. for 30 minutes.
8. Pellet the DNA by centrifuging the sample at full speed for 30 minutes at +4° C.
9. Wash the pellet with 150 µl of 70% ethanol, centrifuge at full speed for 10 minutes dry and resuspend the pellet in 6 µl of ddH2O.
10. Add 4 µl of freshly prepared 10× digestion mix (2.5 µl FastDigest® BglII (Fermentas, CAT #FD0083), 2.5 µl FastDigest® Eco31I (Fermentas, CAT #FD0293), 10 µl FastDigest® Buffer and 25 µl ddH2O) and incubate at 37° C. for 10 minutes.
11. Add RNAse A up to 40 µg/ml and incubate at 37° C. for 10 minutes.
12. Load samples onto a 1.0% agarose gel made with 1×TAE to see if repair has occurred.

Repair percentages are analysed using Image-Pro® 4.0 (Media Cybernetics, Silver Spring, Md., USA).

MMR-proficient HeLa NE is used as a positive control, whereas uncomplemented MMR deficient NEs are used as negative controls. The substrates are linearised with Eco31I restriction enzyme. As the repair reaction converts a GT heteroduplex to an AT homoduplex or fills the 1 or 2 nt loop structures recreating the BglII restriction site, the repair efficiency can be measured by the efficiency of the double digestion.

Example 7. Fibroblast Cells Used in the MMR Assay According to the Present Invention This example was performed to show that the MMR assay can be performed on normal tissue, such as fibroblast cells. Wild-type fibroblast nuclear extract (FB-WT) prepared as described in example 2, nuclear extract from MMR proficient HeLa cells and a negative control (MOCK) containing no proteins were subjected to an MMR assay according to the present invention as described in example 3.

After allowing the repair reaction to take place, a double digestion of the substrate DNA will yield a single larger band of approximately 3000 bp where no repair has occurred, and further two smaller fragments (of approximately 1800 and 1300 bp) where repair has occurred. As the substrate DNA is always added in excess, even MMR proficient extracts will have the linearized substrate present in addition to the double cleavage fragments.

Figure 2:
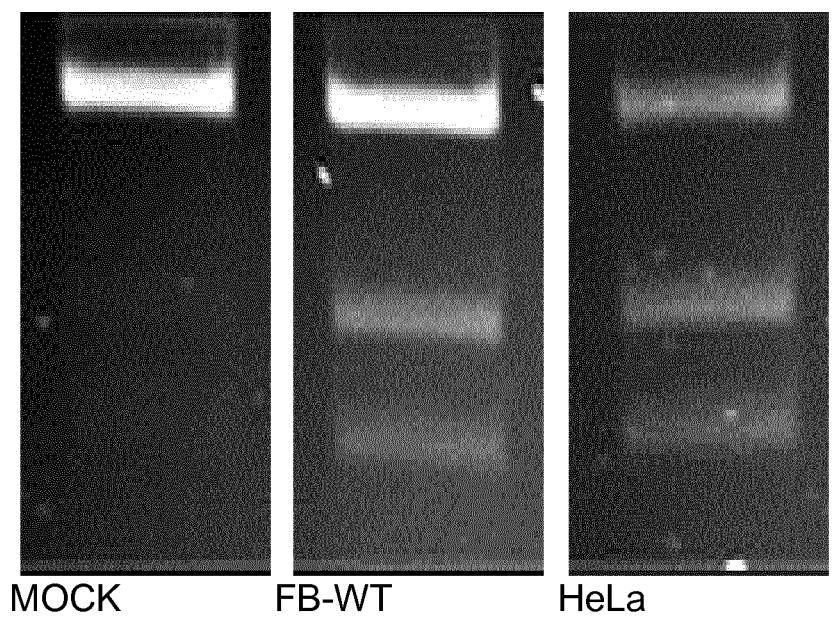
FIG. 2 is an MMR analysis of healthy fibroblast nuclear extract (FB-WT, wild type) compared to that obtained from an MMR proficient cell line (HeLa) and an MMR deficient assay control (MOCK) without nuclear proteins.

The result of this assay is presented in FIG. 2, which shows that lane 1 containing MOCK cells has only one large band (=no repair), whereas lanes 2 and 3, containing FB-WT and HeLa nuclear extracts, respectively, show two additional, smaller bands, indicative of a repair reaction.

Thus, this example unambiguously shows that nuclear extracts from normal fibroblast cells have a MMR capability comparable to that of a MMR proficient control cell line (HeLa), which can be confirmed by an assay according to the present invention.

Example 8. Human Fibroblast Cells with a Partly Silenced MMR Gene Show Decreased MMR Capability in the MMR Assay According to the Present Invention This example shows that human fibroblast cell lines FB-M1 and FB-SH13 (described in example 2), where the MLH1 gene or MSH2 gene, respectively, is partly silenced by (sh)RNA technology, display a clear decrease in MMR capability.

Figure 3:
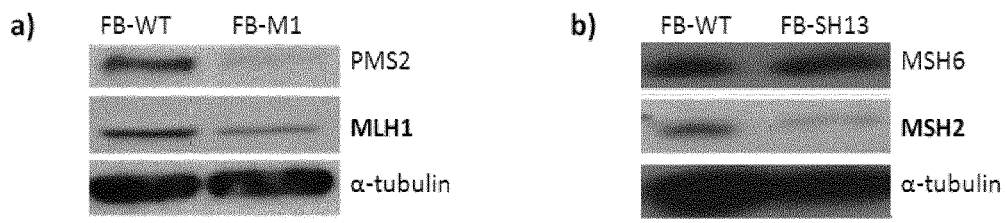
FIG. 3 is a Western blot analysis showing (FIG. 3(a)) the MMR protein content (MLH1 and its counterpart PMS2) of a healthy fibroblast nuclear extract (FB-WT) compared to the fibroblast derivative cell line FB-M1 where MLH1 has been partially silenced and (FIG. 3(b) the MMR protein content (MSH2 and its counterpart MSH6) of FB-WT compared to the fibroblast derivative cell line FB-SH13 where MSH2 has been partially silenced.

Firstly, a Western blot was performed on equal amounts of nuclear extracts from wild-type fibroblast (FB-WT) cells and FB-M1 cells or FB-WT and FB-SH13 cells. As a result (FIG. 3) it can be seen, that the amount of MLH1 protein is clearly decreased in FB-M1 cells as compared to FB-WT, as is the level of MSH2 in FB-SH13 cells. α-tubulin is included as a loading control.

Secondly, the MMR assay was performed as described in example 6, using the same nuclear extracts in equal amounts:

MOCK—Nuclear extract free negative assay control;
FB-WT—Wild type human fibroblast cell nuclear extract (positive control); and FB-M1—Nuclear extract from human fibroblast cells with partly silenced MLH1; or
FB-SH13—Nuclear extract from human fibroblast cells with partially silenced MSH2.

Figure 4:
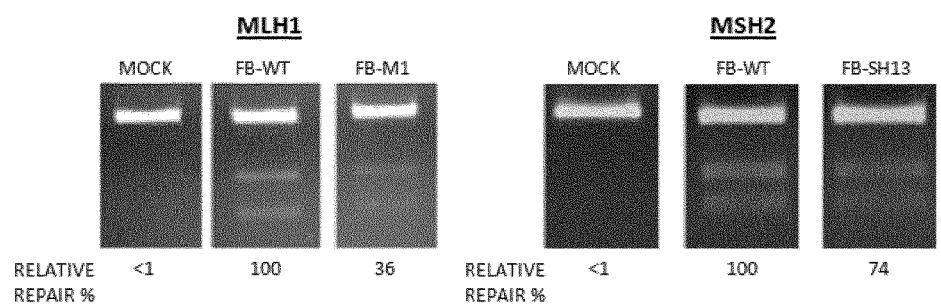
FIG. 4 is a quantitative MMR analysis showing that the deficiency of MLH1 in FB-M1 and MSH2 in FB-SH13 is detected as a decrease in repair efficiency with varying intensity. Relative repair percentages are shown in respect to the repair efficiency of FB-WT.
Figure 5:
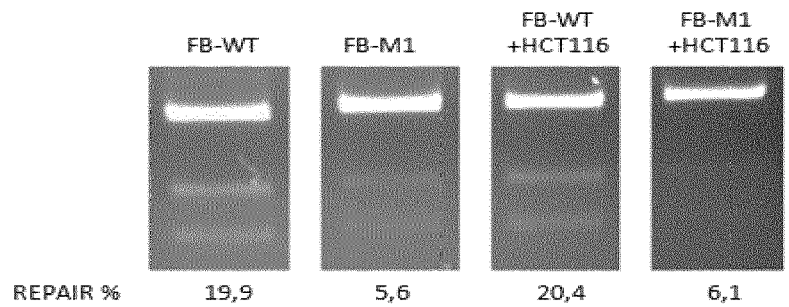
FIG. 5 is a quantitative MMR analysis showing that different MMR capability of FB-WT and FB-M1 can be detected when used in combination with an MLH1 deficient nuclear extract HCT116)

The result of this assay shows that a lowered concentration of one of the key MMR proteins is associated with a defected MMR mechanism. The result is shown in FIG. 4 and it clearly demonstrates that compared to the wild type human fibroblast nuclear extract, the MMR assay according to the present invention detects the deficiency of MLH1 and MSH2 as a decrease in repair efficiency. Furthermore, the MMR capability of an MMR deficient nuclear extract can be differentially restored when assayed together with wild-type or partially MMR deficient nuclear extract as presented in FIG. 5 (HCT116 with FB-WT or FB-M1 in this case) and described by the test presented in Table 1 and described on pages 10-11.

The repair efficiency in the MMR assay according to the present invention is regarded as the percentage of repaired DNA of all substrate DNA in the reaction. The shortage of a key MMR protein reduces the repair efficiency with varying intensity whereas the complete absence of key MMR proteins reduce the repair efficiency to a non-detectable level.

Example 9. A Kit for Use in an Assay for Diagnosing Defects in MMR

A kit according to the present invention is preferably presented as vials preloaded with all reagents for performing the MMR assay. Only test sample nuclear extract is added. In one embodiment of the present invention separate vials for the different MMR deficiencies to be tested are presented.

This example describes a kit for determining whether a subject has Lynch syndrome or not, by determining whether a said subject has a defect in the MLH1 gene or in either of the MSH2 or MSH6 genes, without distinguishing between the latter. Such a kit has at least five separate vials.

TABLE 2

| Vial | Reagent | |
|---|---|---|
| 1 | HCT116 = | MLH1 deficient control NE |
| 2 | LoVo = | MSH2/6 deficient control NE |
| 3 | HCT116 = | to be complemented by sample NE |
| 4 | LoVo = | to be complemented by sample NE |
| 5 | FB-WT = | MMR proficient NE, positive control |

The reagents included in said vials are:
Substrate Heteroduplex
Nuclear extract (HCT116, LoVo or FB-WT)
10X MMR buffer (200 mM Tris-HCL pH 7.6, 400 mM KCl, 50 mM MgCl2, 10 mM Glutathione, BSA 500 µg/ml, 1 mM each dNTP, 15 mM ATP).

In addition to this, a STOP solution for MMR assay (42 mM EDTA, 1.2% SDS, 50.4 µg/ml Proteinase K) is required, and could thus be provided with the kit.

Furthermore, said kit may, optionally, contain reagents required for clarifying the sample (TE buffer, phenol/chloroform/isoamyl alcohol and chloroform), for precipitating it (NaCl and ethanol) and for detecting the repair (RNase A and restriction enzymes BglII and Eco31I with buffer and loading dye).

Further optional components of the kit are reagents required for the culturing of the cells the sample nuclear proteins are to be extracted from as well as the reagents required for the extraction of the nuclear proteins from it (see example 2).

A kit according to the present invention is not restricted to any specific form or type of vials. Any type of vials suitable for handling and incubations as described in example 6, such as Eppendorf® tubes are suitable.

The invention claimed is:

1. An in vitro method for determining whether a human subject has a DNA mismatch repair (MMR) function, the method comprising:
   a) producing a primary fibroblast cell nuclear protein extract from cultured primary fibroblast cells derived from a normal constitutive tissue sample obtained from a human subject;
   b) providing at least one MMR proficient nuclear protein extract (MMR+/+) as a positive control and at least one MMR deficient nuclear protein extract (MMR−/−) as a negative control;
   c) combining the primary fibroblast cell nuclear protein extract with at least one mismatch-bearing heteroduplex DNA substrate, the MMR proficient nuclear protein extract with the at least one mismatch-bearing heteroduplex DNA substrate and MMR deficient nuclear protein extract with the at least one mismatch-bearing heteroduplex DNA substrate in different separate vials;
   d) after step c), performing a mismatch repair assay in each of the separate vials, resulting in repaired heteroduplex DNA substrate molecules and/or unrepaired heteroduplex substrate DNA molecules in each of the separate vials; and
   e) calculating repair efficiencies of the primary fibroblast cell nuclear protein extract, the MMR proficient nuclear protein extract and MMR deficient nuclear protein extract on said at least one mismatch-bearing heteroduplex DNA substrate by determining a quantity of the repaired heteroduplex DNA substrate molecules and a quantity of the unrepaired heteroduplex molecules resulting from the mismatch repair assay in each of the separate vials after step d), thereby determining whether the human subject has a DNA mismatch repair function based on a comparison of said repair efficiencies.

2. The method according to claim 1, wherein the at least one mismatch-bearing heteroduplex DNA substrate is derived from a plasmid having SEQ ID NO: 1.

3. The method according to claim 2, wherein the at least one mismatch-bearing heteroduplex DNA substrate further comprises a nucleic acid sequence selected from the group consisting of SEQ ID NO:2 and SEQ ID NO:3.

4. An in vitro method for determining whether a human subject has a DNA mismatch repair (MMR) function, the method comprising:
   a) producing a primary fibroblast cell nuclear protein extract from cultured primary fibroblast cells derived from a normal constitutive tissue sample obtained from a human subject;
   b) providing at least one MMR proficient nuclear protein extract (MMR+/+) as a positive control and at least one MMR deficient nuclear protein extract (MMR−/−) a negative control;
   c) mixing the at least one MMR deficient nuclear protein extract with the primary fibroblast cell nuclear protein extract, thereby forming a mixed nuclear protein extract;
   d) combining the primary fibroblast cell nuclear protein extract with at least one mismatch-bearing heteroduplex DNA substrate, the MMR proficient nuclear protein extract with the at least one mismatch-bearing heteroduplex DNA substrate, MMR deficient nuclear protein extract with the at least one mismatch-bearing heteroduplex DNA substrate, and the mixed nuclear protein extract with the at least one mismatch-bearing heteroduplex DNA substrate in different separate vials;
   e) after step d), performing a mismatch repair assay on each of the separate vials, resulting in repaired heteroduplex DNA substrate molecules and/or unrepaired heteroduplex substrate DNA molecules in each of the separate vials; and
   f) calculating repair efficiencies of the primary fibroblast cell nuclear protein extract, the MMR proficient nuclear protein extract, MMR deficient nuclear protein extract and the mixed nuclear protein extract on said at least one mismatch-bearing heteroduplex DNA substrate by determining a quantity of the repaired heteroduplex DNA substrate molecules and a quantity of the unrepaired heteroduplex molecules resulting from the mismatch repair assay in each of the separate vials after step e), thereby determining whether the human subject has a DNA mismatch repair function based on a comparison of said repair efficiencies.

* * * * *